United States Patent
Li et al.

(10) Patent No.: US 6,780,423 B1
(45) Date of Patent: Aug. 24, 2004

(54) ADHESIVE-RESISTING SKIN PROCESSING AGENT FOR PVC POWDER FREE GLOVES

(76) Inventors: Chin Tai Li, No. 44, Chaishan, Taoyuan Li, Gushan Chiu, Kaohsiung (TW), 804; Hui Hua Yang, No. 18, Lane 177, Dungsheng Rd., Shinying City, Tainan (TW), 730

( * ) Notice: Subject to any disclaimer, the term of this patent is extended or adjusted under 35 U.S.C. 154(b) by 0 days.

(21) Appl. No.: 10/437,790

(22) Filed: May 14, 2003

(51) Int. Cl.[7] .......................... A01N 25/34; A61K 33/00
(52) U.S. Cl. ........................................ 424/402; 424/724
(58) Field of Search .................................. 424/402, 724

(56) References Cited

U.S. PATENT DOCUMENTS

| | | |
|---|---|---|
| 5,881,386 A | 3/1999 | Horwege et al. |
| 6,274,154 B1 | 8/2001 | Chou |
| 6,423,328 B2 | 7/2002 | Chou |

Primary Examiner—Alton N. Pryor
(74) Attorney, Agent, or Firm—Alan D. Kamrath; Nikolai & Mersereau, P.A.

(57) ABSTRACT

An adhesive-resisting skin treatment agent for PVC gloves is produced when the glove mold is soaked in a PVC or PVC polymer and a plastisol to form a film after cooling. The gloves are soaked in a polymer adhesive-resisting treatment solution primarily consisting of chitin, trioctanoin, an aqueous polyester resin and an aerosol mixed in a certain proportion. The capillary and the surface of the film on the gloves can absorb such solution and is evenly coated with a film. Thereafter, the gloves are cooled and their edges are rolled up and detached from the mold. The inner surface of the coating has a protective film and gives a soft, smooth, and comfortable feeling to the wearer's hand when such inner surface is in contact with the hand. Furthermore, the heat of the sweat produced after wearing the gloves for a long time can release the chitin and trioctanoin in the capillary or the surface of the inner side of the gloves and accomplish the effect of protecting the wearer's skin

3 Claims, No Drawings

ADHESIVE-RESISTING SKIN PROCESSING AGENT FOR PVC POWDER FREE GLOVES

FIELD OF INVENTION

The present invention introduces an organic denatured chitin and a trioctanoin having moisture-proof and lubricating functions to produce a stable aqueous processing agent so that such agent can be evenly attached on the surface of the gloves and the chitin and trioctanoin are dissolved by the action of sweat and body temperature to form a moist, wet, and skin protective layer on the hand.

BACKGROUND OF THE INVENTION

General soft and waterproof gloves are necessary tools for medical treatments. Traditionally, gloves usually use natural latex as the raw material and are produced after the formation and sulfur addition processes. Since natural latex has a blocking property, cornstarch or chloride are used to remove the stickiness in order to facilitate mold separation and user's wear. However, besides the high price, natural rubber gloves contain natural allergic sources that may cause allergies easily, and constitute a burden to the health of skin for these who wear gloves for a long time.

Soft PVC gloves are made by a plastisol composed of PVC (polyvinyl chloride) powder, a plastic agent, and a manufacturing agent, after going through the soaking emulsification processes in a ceramic mold to produce soft gloves similar to those formed of latex. The soft PVC gloves also have a strong sticky property, and thus cornstarch is used to remove the stickiness. A latex made of polyester aqueous PU (polyurethane), a rough surface agent, and a lubricant as disclosed in the U.S. Pat. No. 5,881,386 is used to substitute the cornstarch, so that the gloves produced will not have powder pollution. Since this polymer coating has a lubricating property and rough surface, the gloves can be separated from the mold and worn easily. However, long time wear may easily dry the skin and cause discomfort. Therefore, the method disclosed in U.S. Pat. Nos. 6,274,154 and 6,423,328 is to dip the gloves into aloe vera, which has the functions of moist-proofing and skin protection, and thus provides a protective effect to the skin of the hand when wearing such gloves.

However, since the surface of PVC gloves is water repellent and aloe vera is an aqueous solution, it is unable to coat the aloe vera evenly on the surface of the gloves without adding interface activators. Moreover, the layer coated with aloe vera does not have sufficient stickiness resistance. Therefore after the mold of the gloves is turned over for peeling, the inner sides of the gloves will stick together. The aloe vera is actually not suitable for powder free soft PVC gloves.

Further, a traditional polymer powder free stickiness resisting agent composed of a binder (such as aqueous acrylic resin or aqueous PU resin), a filler (such as silicon dioxide and an interface activator), a thickener, a lubricant (such as organic silicon alkane and paraffin), and a foam eliminator can be used for dipping the stickiness-proof second layer of the gloves. However, wearing the gloves for a long time makes the skin on hands dry. Such dipping solution contains several organic ingredients, and thus germs will breed easily and spoil the gloves. To improve the above situations, some people add a disinfectant for germ breeding prevention. However, the disinfectant remaining on the hand also causes discomfort (or allergies) to the human body or even endangers health after wearing the gloves for a long time.

SUMMARY OF THE INVENTION

The primary objective of the present invention is to provide an adhesive-resisting skin treatment agent for PVC gloves. Particularly the gloves' mold is soaked in a PVC or PVC polymer and a plastisol to form a film after cooling. Then, the gloves are soaked in a polymer adhesive-resisting treatment solution primarily including chitin, trioctanoin, aqueous polyester resin and aerosol mixed in a certain proportion. Therefor, the capillary and the surface of the film on the gloves can absorb such solution and is evenly coated with a film. Thereafter, the gloves are cooled, and their edges are rolled up and detached from the mold. The inner surface of the coating has a protective film and gives a soft, smooth, and comfortable feeling to the wearer's hand when such inner surface is in contact with the hand. Furthermore, the heat of the sweat produced after wearing the gloves for a long time can release the chitin and trioctanoin in the capillary or the surface of the inner side of the gloves, accomplishing the effect of protecting the wearer's skin.

DETAILED DESCRIPTION OF THE PREFERRED EMBODIMENTS

Therefore, to improve powder-free gloves so that they will not stick to the wearer's hand but will provide comfortable and maintenance functions, the gloves' mold is soaked in a PVC or PVC polymer and a plastisol to form a film after cooling. Then, the gloves are soaked in a polymer adhesive-resisting treatment solution primarily consisting of chitin, trioctanoin, aqueous polyester resin and aerosol mixed in a certain proportion. The capillary and the surge of the film on the gloves can absorb such solution and is evenly coated with a film. Thereafter, the gloves are cooled, and their edges are rolled up and detached from the mold. The inner surface of the coating has a protective film and gives a soft, smooth, and comfortable feeling to the wearer's hand when such inner surface is in contact with the hand. Furthermore, the heat of the sweat produced after wearing the gloves for a long time can release the chitin and trioctanoin in the capillary or the surface of the inner side of the gloves, accomplishing the effect of protecting the wearer's skin.

In the meantime, since the stickiness resisting skin treatment agent soaked in the inner side of the gloves has excellent stickiness resistance and is slippery and after the mold of the gloves is turned over for peeling, the inner sides of the gloves will not stick together.

Thus, the present invention can be implemented by the embodiment as described above. However, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

The method of manufacturing PVC powder free gloves according to the present invention is made of a plastisol with the recipe of PVC powder, a plastic agent, and a manufacturing agent. A ceramic mold is soaked into such plastisol solution so that a film is attached on the surface of such mold. After the film is cooled and dried, the mold is soaked into an emulsion of processing agent for a period of time to attach another stickiness resisting skin care film on top of the original film attached on the mold. After the film is dried, the glove so formed on the mold can be turned over and peeled. Finally, a powder free glove having a stickiness proof skin protective film is obtained, and the composition of the aforementioned processing agents is given as follows:

Solid polyester aqueous PU of about 25% by weight is used as a cohesive agent; silicon dioxide of about 4.8% by weight acts as an aerosol; organic denatured silicone of about 1% by weight acts as an interface activator for the coating of the stickiness-proof agent; a PU thickener of about 1.9% by weight is used to adjust the stickiness of the stickiness resisting agent; an organic denatured chitin of about 48% by weight and water of about 19.3% by weight are used for the dilution and composition of the mixture as shown in Table 1:

TABLE 1

| Source | Trade name | Weight (gram) |
|---|---|---|
| U-Glory | UGthane ®996 | 20 |
| Degussa | Aersoil ®R972 | 5 |
| Byk-Chemie | BYK ®346 | 1 |
| Solutia | Addiltol VXW6360 | 2 |
| Ichimaru Pharcos | Chitin Liquid-HV | 50 |
| Patech | Paester ®9306 | 2 |
|  | Water | 20 |

Alternatively, solid polyester aqueous PU of about 25.2% by weight acting as a cohesive agent; silicon dioxide of about 4.9% by weight acting as an aerosol; an organic denatured silicone of about 1% by weight acts as an interface activator for the coating of the stickiness-proof agent; a PU thickener of about 1.9% by weight is used to adjust the stickiness of the stickiness resisting agent; trioctanoin of about 2.9% by weight and water of about 64.1% by weight are used for the dilution and composition of the mixture as shown in Table 2.

TABLE 2

| Source | Trade name | Weight (gram) |
|---|---|---|
| U-Glory | Ugthane ®996 | 25 |
| Degussa | Aersoil ®R972 | 4.8 |
| Byk-Chemie | BYK ®346 | 1 |
| Solutia | Addiltol VXW6360 | 1.9 |
| Ichimaru Pharcos | Chitin Liquid-HV | 48 |
| Patech | Paester ®9306 | 19.3 |
|  | Water | 25 |

Alternatively, solid polyester aqueous PU of about 20% by weight acting as a cohesive agent; silicon dioxide of about 5% by weight acting as an aerosol; an organic denatured silicone of about 1% by weight acts as an interface activator for the coating of the stickiness-proof agent; a PU thickener of about 2% by weight is used to adjust the stickiness of the stickiness resisting agent; trioctanoin of about 2% by weight and water of about 20% by weight are used for the dilution and composition of be mixture as shown in Table 3.

TABLE 3

| Source | Trade name | Weight (gram) |
|---|---|---|
| U-Glory | UGthane ®996 | 25.2 |
| Degussa | Aersoil ®R972 | 4.9 |
| Byk-Chemie | BYK ®346 | 1 |
| Solutia | Addiltol VXW6360 | 1.9 |
| Ichimaru Pharcos | Chitin Liquid-HV | 2.9 |
| Patech | Paester ®9306 | 64.1 |
|  | Water | 25.2 |

Therefore, the chitins also known as chitosan which is the water soluble high polymer extracted from the shell of the crustacean, has a structure similar to the cellular structure on the inner side of the gloves and has the functions of moisture preservation and skin protection as well as the antiseptic function, so that the gloves can be preserved over a long period of time without getting rotten easily. The trioctanoin also has good moisture preservation functions. Thus, the high polymer powder free stickiness resisting agent is made by the chitin, trioctanoin, and polyester aqueous PU. The ceramic mold is soaked into a PVC plastisol to form a first layer of film. The gloves are soaked into a high polymer stickiness-resisting agent containing either chitin or trioctanoin, or both, forming a second layer of stickiness resisting protective film on the inner side of the glove. Such stickiness resisting agent has good adhesion with the first PVC layer, so that the stickiness resisting protective film will not come off easily during mold separation and wearing, and will not produce any powder. In the meantime, since the stickiness resisting skin treatment agent soaked in the inner side of the gloves has excellent stickiness resistance and is slippery and after the mold of the gloves is turned over for peeling, the inner sides of the gloves will not stick together. Furthermore, when the wearer wears the gloves, the chitin and trioctanoin is dissolved by the action of sweat and body temperature to form a moist, wet, and skin protective layer on the hand. When the wearer removes the gloves, the hand will have a smooth and slippery feeling, which has the effect of protecting skin and providing a protective effect to those wearing the gloves for a long time. Traditional processing agents cannot accomplish such effects.

Thus, soaking the gloves of the present invention into the processing agent containing chitin or trioctanoin for the second time will coat a layer similar to the cellular structure on the inner side of the gloves so that the gloves have slippery, antiseptic, moisture preservation and skin protection effects. The present invention has effects that cannot be accomplished by the prior art processing method.

What is claimed is:

1. An adhesive-resisting skin treatment agent for polyvinyl chloride powder-free gloves, wherein said agent is comprised of a mixture of polyurethane 15–60% by weight, silicon dioxide 1–10% by weight, an organic denatured silicone 0.5–3% by weight, a thickener 1–5% by weight, chitin 10–50% by weight, and water 15–65% by weight.

2. An adhesive-resisting skin treatment agent for polyvinyl chloride powder-free gloves, wherein said agent is comprised of a mixture of polyurethane 15–60% by weight, silicon dioxide 1–10% by weight, an organic denatured silicone 0.5–3% by weight, a thickener 1–5% by weight, trioctanoin 1–10% by weight, and water 15–65% by weight.

3. An adhesive-resisting skin treatment agent for polyvinyl chloride powder-free gloves, wherein said agent is comprised of a mixture of polyurethane 15–60% by weight, silicon dioxide 1–10% by weight, an organic denatured silicone 0.5–3% by weight, a thickener 1–5% by weight chitin 10–50% by weight, trioctanoin 1–10% by weight, and water 15–65% by weight.

* * * * *